(12) United States Patent
Domb

(10) Patent No.: US 6,514,522 B2
(45) Date of Patent: Feb. 4, 2003

(54) POLYMER CONSTRUCTS

(75) Inventor: Abraham J. Domb, Efrat (IL)

(73) Assignee: Chondros, Inc., Towson, MD (US)

( * ) Notice: Subject to any disclaimer, the term of this patent is extended or adjusted under 35 U.S.C. 154(b) by 0 days.

(21) Appl. No.: 09/929,697

(22) Filed: Aug. 14, 2001

(65) Prior Publication Data

US 2002/0012705 A1 Jan. 31, 2002

Related U.S. Application Data

(60) Provisional application No. 60/081,016, filed on Apr. 8, 1998, provisional application No. 60/104,842, filed on Oct. 20, 1998, provisional application No. 09/275,319, filed on Mar. 24, 1999, provisional application No. 60/165,608, filed on Nov. 15, 1999, and provisional application No. 60/228,855, filed on Aug. 29, 2000.

(51) Int. Cl.[7] .............................. A61K 9/70; A61K 9/16; A61K 9/50; A61K 47/48
(52) U.S. Cl. ..................... 424/443; 424/493; 424/78.17
(58) Field of Search ................................ 424/493, 443, 424/78.17, 197.11

(56) References Cited

U.S. PATENT DOCUMENTS

| 4,553,272 A | 11/1985 | Mears ........................... 623/1 |
| 4,757,017 A | 7/1988 | Cheung ................. 435/240.23 |
| 5,041,138 A | 8/1991 | Vacanti et al. ................. 623/16 |
| 5,258,028 A | 11/1993 | Ersek et al. .................... 623/11 |
| 6,156,320 A | * 12/2000 | Izvekova et al. ...... 424/197.11 |
| 6,197,061 B1 | 3/2001 | Masuda et al. .......... 623/11.11 |
| 6,214,331 B1 | * 4/2001 | Vanderhoff et al. ...... 424/78.17 |

FOREIGN PATENT DOCUMENTS

WO        WO 97/41899        * 11/1997

* cited by examiner

Primary Examiner—Thurman K. Page
Assistant Examiner—Blessing Fubara
(74) Attorney, Agent, or Firm—Armstrong, Westerman & Hattori, LLP

(57) ABSTRACT

Polysaccharide polymers are employed in various medical applications. For example, chitosan—arabinogalactan and polysaccharide amine polymers are disclosed. The polymers can be used to prevent wound adhesion, to provide scaffolds for tissue transplantation and carriers for cell culture.

9 Claims, 4 Drawing Sheets

POLYMER CONSTRUCTS

RELATED APPLICATIONS

This application is related to provisional applications Ser. No. 60/081,016 filed Apr. 8, 1998 and Ser. No. 60/104,842 filed Oct. 20, 1998; patent application Ser. No. 09/275,319 filed Mar. 24, 1999, provisional application No. 60/165,608 filed Nov. 15, 1999 and provisional application No. 60/228,855 filed Aug. 29, 2000.

FIELD OF THE INVENTION

The invention is involved with making improved polymers and compositions employing these polyers.

BACKGROUND OF THE INVENTION

The herein disclosed invention is concerned with making improved polymer compositions for use as scaffolds for incorporating cells to be used for tissue repair. The invention is also concerned with making improved polymer compositions for use as agents to prevent tissue adhesion after surgery and as wound healing agents. The polymer compositions can also be used as aids to cell culture.

OBJECTS OF THE INVENTION

An object of this invention is to produce polymer constructs upon which cells can be cultured.

A main object of this invention is to prepare polymer scaffolds on which cells can be grown and thereafter used as tissue replacements.

A further object of this invention is to produce devices such as films, sheets or powders for preventing tissue adhesion. Examples of surgery requiring tissue adhesion prevention are gynecological and abdominal surgery.

An object of this invention is to produce polymer compositions useful as wound healing agents.

These and other objects of the present invention will become apparent from a reading of the following specification taken in conjunction with the enclosed drawings.

SUMMARY OF THE INVENTION

The herein disclosed invention encompasses an overall process starting with a method of obtaining cells such as chondrocytes, preparing the chondrocytes for transplantation and then actually transplanting them. The invention can be conceptualized as being divided into various phases. These phases can generally be identified as follows:

Phase I

Phase I of this invention involves an elegant and efficient method of obtaining cartilage from which there is to be obtained chondrocytes. The herein disclosed invention covers not only the obtaining of cartilage from conventional sources, but also cartilage from the nose.

Phase II

This phase involves obtaining a sample of cartilage as the source of chondrocytes; then deriving chondrocytes from said cartilage.

The obtaining of cells and cell sources such as stromal cells and stem cells are contemplated as being part of this phase of the invention.

Phase III

This phase involves culturing cells and particularly chondrocytes, so as to obtain optimum amounts and optimum quality of cells by monitoring culture conditions. The conditions to be monitored would involve for example:

1) The spin rate and conditions of spin.
2) Type of microcarrier or microbeadlet producing optimum results.
3) The culture media producing optimum growth of good quality chondrocytes or cells.
4) The temperature during culture.
5) The pressure employed during culture.
6) Amount of oxygen employed during culture.
7) Amount of $CO_2$ employed during culture.
8) Degree of Integrin expression.
9) The phenotype of chondrocytes.
10) Optimum concentration of cells in culture, e.g., removing cells to retain an optimum concentration of cells during culture.
11) Replenish culture media.
12) Ascertain that cells are producing proper metabolic by-products.
13) Electro-magnetic stimulation.
14) Addition of growth factors to the culture media, e.g. TGF.
15) Varying culture conditions for chondrocytes between spin-culture, surface culture and stretch culture.
16) Pressure and mechanical strain.

An important aspect of the cell culture of this invention comprises optimizing the production of cells, e.g chondrocytes by a servo controlled mechanism which has been perfected to control culture conditions so as to produce optimum quantities and qualities of cells.

It is to be understood that these culture techniques are not only applicable to chondrocytes, but also to other cells such as osteoblasts and stem cells.

Phase IV

This phase involves preparing scaffold material and microcarriers upon which cells are to be grown and then transplanted as a prosthesis; particularly chondrocytes on a scaffold are to be used for cartilage repair or replacement. The scaffold material will take the shape of the body part to be replaced, and further the scaffold material can, for example, be in the form of a mesh, sponge or like porous body. Various polymers such as polysaccharide polymers are envisioned as being operative in this invention.

Phase V

This phase involves preparing a cell-implanted scaffold. Once the scaffold per se is obtained in its proper shape, it can be cultured along with chondrocytes to prepare a prosthesis for cartilage repair. Special culture techniques, such as the application of pressure, are visualized as being necessary for proper manufacture of the cell implanted scaffold.

Phase VI

This phase embraces surgical techniques for implanting the scaffold for cartilage repair or repair of other body defects such as skin, etc. Not only are humans to be surgically treated by the methods of this invention, but also animals such as horses.

Phase VII

In carrying out the procedures of this invention, FDA guidelines will be followed. Tests and methods for improving and complying with regulatory guidelines are to be advanced.

Phase VIII

This invention also embraces a phase in which polymer constructs are prepared and used as tissue-adhesion prevention agents, polymer constructs on which cells are grown and constructs used for wound-healing and tissue repair.

The herein disclosed invention embraces use mainly culturing cells, Phase III; preparing scaffold material, Phase IV; preparing scaffold, Phase V and polymer constructs used for tissue adhesion prevention and cell culture, Phase VIII.

DEFINITION OF TERMS

AG=Arabinoglactan
PLA=poly (lactide)
PLGA=poly (lactide—glycolide)

DESCRIPTION OF THE INVENTION

1. Preparation of Microspheres

Synthesis of Chitosan—Arabinopalactan Crosslinked Spheres

Figure 1:
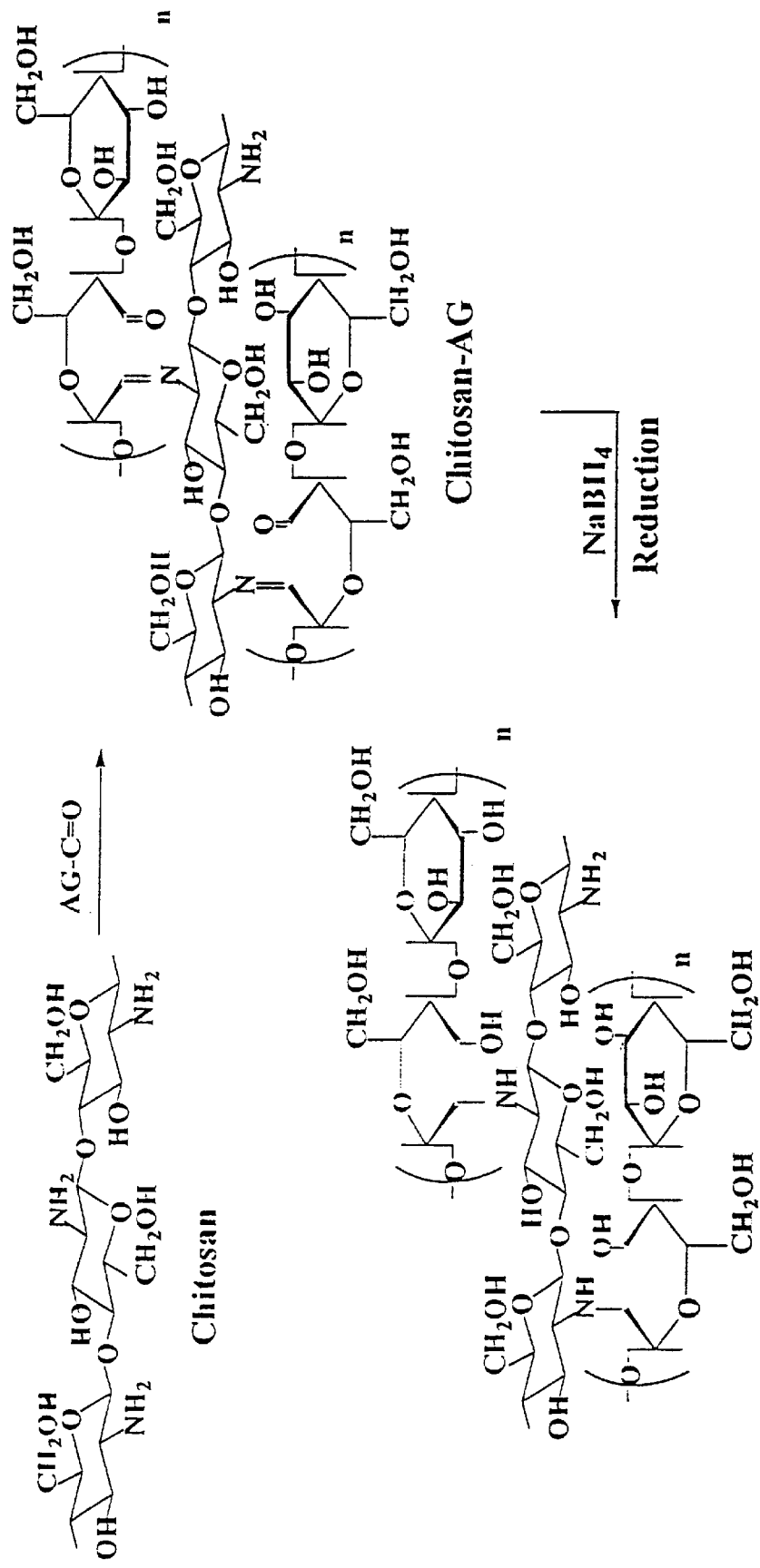
FIG. 1 describes chemical reactions between chitosan and arabinogalactan (AG).
Figure 2:
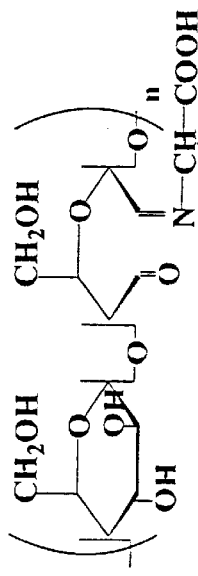
FIG. 2 describes the reaction product of arabinogalactan (AG) and lysine; and the reaction product between arabinogalactan and gelatin.
Figure 2:
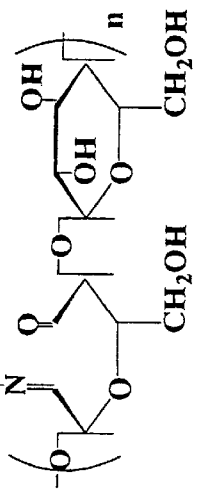
Figure 2:
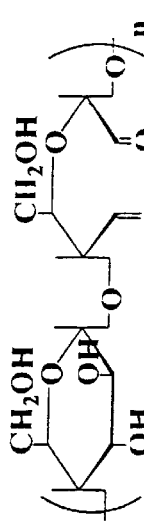
Figure 2:
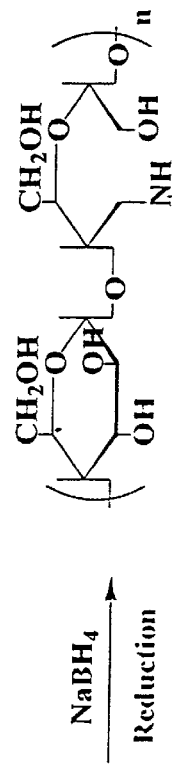
Figure 2:
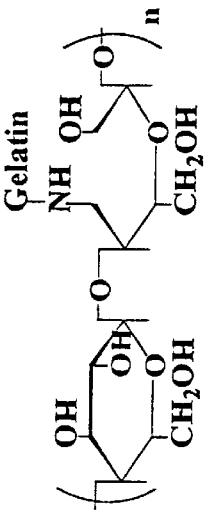
Figure 3:
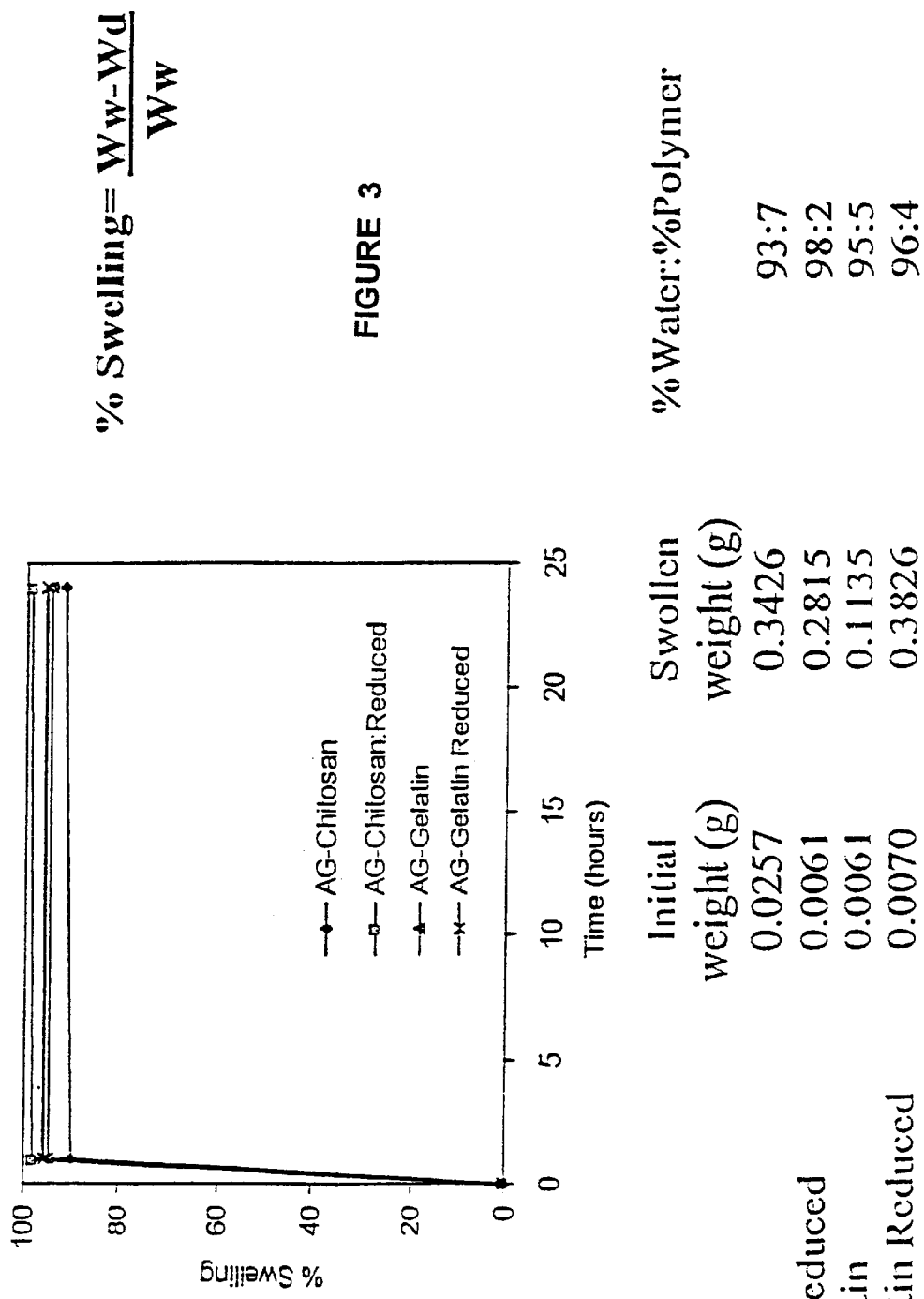
FIG. 3 is a chart describing swelling times of various arabinogalactan gels.
Figure 4:
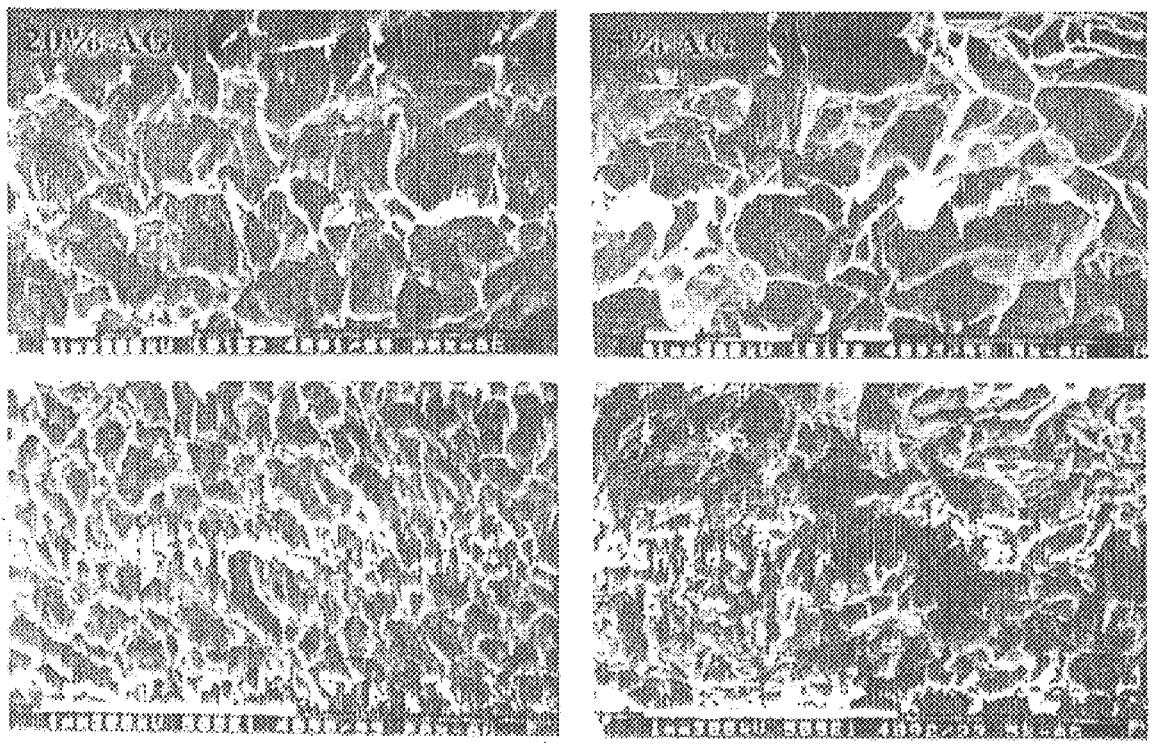
FIG. 4 are scanning election micrographs of chitosan-arabinogalactan sponges.

P2TE-58: A 4% solution of chitosan in 5% aqueous acetic acid containing 2% NaCl was prepared, and 6 g of this solution was dispersed in a mixture of 35 ml of liquid paraffin and 25 ml of petroleum ether containing 1 g ($1.05 \times 10^{-3}$ mole) of sorbitan-trioleate (arlacel 85, HLB=1.8) at room temperature. The dispersion was stirred at 2000 rev/min for 15 min. A solution of 0.1 g oxidized AG in 3 ml Borate buffer pH=8.5 was prepared. This solution was added to the Chitosan dispersion at a rate of 1 ml every 15 minutes. The stirring was continued overnight. At the end of the reaction, the hardened particles were washed 3 times with petroleum-ether, followed by methanol, and finally with acetone. The particles were air dried for a few hours at room temperature.

Result: Powder with a pink color is obtained with particle size of 200 to 400 microns which swells well in culture media.

P2TE-64: A 4% solution of chitosan in 5% aqueous acetic acid containing 2% NaCl was prepared, and 6 g of this solution was dispersed in a mixture of 35 ml of liquid paraffin and 25 ml of petroleum ether containing 0.8 g ($2.3 \times 10^{-3}$ mole) of sorbitan-monolaurate (span 20, HLB=8.6) at room temperature. The dispersion was stirred at 2000 rev/min for 15 min. A solution of 0.1 g oxidized AG in 3 ml Borate buffer pH=8.5 was prepared. This solution was added to the Chitosan dispersion at a rate of 1 ml every 15 minutes. The stirring was continued overnight. At the end of the reaction, the hardened particles were washed 3 times with petroleum-ether, followed by methanol, and finally with acetone. The particles were air dried for a few hours at room temperature.

Result: Powder with orange-pink color is obtained with particle size of about 300 microns which swells well in culture media.

P2TE-68: A 4% solution of chitosan in 5% aqueous acetic acid containing 2% NaCl was prepared, and 6 g of this solution were mixed with a mixture of 35 ml of liquid paraffin and 25 ml of petroleum ether containing 0.43 g ($1.05 \times 10^{-3}$ mole) of sorbitan-monostearate (span 60, HLB=4.7) dissolved in 2 ml chloroform, at room temperature. The dispersion was stirred at 2000 rev/min for 15 min. A solution of 0.1 g oxidized AG in 3 ml Borate buffer pH=8.5 was prepared. This solution was added to the Chitosan dispersion at a rate of 1 ml every 15 minutes. The stirring was continued overnight. At the end of the reaction, the hardened particles were washed 3 times with petroleum-ether, followed by methanol, and finally with acetone. The particles were air-dried for a few hours at room temperature.

Result: Powder with orange-pink color is obtained with particle size of about 400 microns which swells well in culture media.

P2TE-65: A 4% solution of chitosan in 5% aqueous acetic acid containing 2% NaCl was prepared, and 6 g of this solution were mixed with a solution of 0.1 g oxidized AG in 2.5 ml Borate buffer pH=8.5. The chitosan-AG mixture was dispersed in a mixture of 35 ml of liquid paraffin and 25 ml of petroleum ether containing 1 g ($1.05 \times 10^{-3}$ mole) of sorbitan-trioleate (arlacel 85, HLB=1.8) at room temperature. The dispersion was stirred at 2000 rev/min overnight. At the end of the reaction, the hardened particles were washed 3 times with petroleum-ether, followed by methanol, and finally with acetone. The particles were air-dried for a few hours at room temperature.

Result: Powder with orange color is obtained with particle size of about 400 microns which swells well in culture media.

The particle size, water content and pore size of the spheres can be controlled by changing the reaction conditions by changing the amount and properties of the surfactant, the pH and ionic strength of the reaction medium, the rate of the addition of the aqueous media to the oil phase and the rate of mixing.

2. Modification of Polysaccharide Matrices

The matrices prepared from the reaction of oxidized polsaccharide and a polyamine can be modified by chemical modification or by physical modification as described below. The starting materials for the preparation of the matrices are oxidized polysaccharides at various degree of oxidation (including: dextran, arabinogalactan, pullulan, cellulose, amylose at an oxidation degree from 5% to about 50% of the saccharide groups) reacted with a polyamine such as a protein, amino containing polysaccharides, and synthetic polyamines including: gelatin, collagen, fibrinogen, fibrin, albumin, hydrolyzed proteins, chitosan, poly(ethylene imine), and poly(vinyl amine). The reaction is usually performed in a buffer solution at 37° C. for 8 to 24 hours. The pH of the reaction can vary from about 5 to about 12 and at an ionic strength between 0.001M up to about 2M. The matrices can be prepared in different shapes including slabs, rods, sheets, thin films, millimeter size beads, microparticles and microspheres.

The matrices can be further modified by physically coating or binding of the matrices by dipping or immersing the matrices in an organic or aqueous solutions of a desired material or materials which after solvent evaporation the additive will remain physically attached to the matrix. The additives that are attached to the matrix construct may alter the hydrophobicity/hydrophilicity of the construct, add functional groups to the construct surface such as amino, hydroxyl, or carboxylic groups that may improve the attachment properties of the matrix to certain types of cells or induction of tissue growth.

A hydrophobic biodegradable coating can be prepared by immersing the matrix in a solution of a hydrophobic biodegradable polymer in an organic solution which after solvent evaporation an adherent coating of the construct structure is obtained. The loading of polymeric material can vary from about 1% by weight of the construct to about 70% of the weight of the coated construct. As the amount of the loaded polymer increases its properties are more pronounced in the final product which also may affect the particle size, the pore size, the water rate and degree of absorption, rate of degradation and elimination of the matrix, and cell attachment and growth properties.

Typically, solutions of biodegradable polymers in the proper organic solvent are prepared at concentrations of about 0.5% w/v to about 10% w/v. Polymers including: lactide-glycolide homopolymers and copolymers, polycaprolactone, polyhydroxybutyrate, polytrimethylene carbonate, poly(dioxepan-2-one), polyanhydrides, polyphosphate esters, polyphosphazenes, polycyanoacrylates, polyorthoesters, and their block or random copolymers with molecular weights ranging from 1,500 daltons to about 500,000 daltons are suitable for this application. The polymer solutions in typical solvents such as: alcohols, acetonitrile, ketones, hydrocarbons, esters, chlorinated hydrocarbons, and ethers are prepared. The preferred solvents are those that are less toxic such as ethanol, propanol, butanol, propylene glycol, acetone, methyl ethyl ketone, ethyl acetate, ethyl lactate, methyl lactate, N-methyl pyrrolidone (NMP), and glycofurol. If solvents such as chloroform and dichloromethane are used, the removal of the solvent to a very low amount (ppm levels) should be considered. The method of applying the polymers on the constructs include dipping the construct in the polymer solution for a few seconds or minutes and evaporating the solvent; immersing the construct in the solution for minutes to hours and then removing from the solution and drying the solvent; spraying the polymer solution onto the construct, this may provide a coating of the polymer more on the surface and less into the core which might be useful for certain cell growth applications.

Hydrophilic small and large molecules may be absorbed on the construct surface by immersing the construct in a solution of the desired molecule either in an organic solvent or in an aqueous solution. For example, to increase the hydrophobicity, a solution of fatty derivatives in an organic solvent is applied (i.e. fatty acid, fatty alcohols, fatty amines, fatty acid esters, triglycerides, fats and waxes). To add hydrophilic properties, polyethylene glycols of molecular weights of between 200 to about 10,000 in acetone, dichloromethane, or water are applied. Other polysaccharides and modified polysaccharides can also be applied by this method using either organic or aqueous solutions. The amount and the effect of these coatings can be evaluated by means used in organic and polymer chemistry including: elemental analysis, surface spectral and masspectrometry measures, differential scanning colorimetry, and electron microscope. The cell growth properties are monitored by seeding the coated construct with certain types of cells and follow their development in vitro and in vivo. The degradation and elimination in vitro are evaluated by immersing the construct in physiological buffer solution and monitoring the leach-out of degradation products and weight loss.

Chemical modification of the matrices can be obtained by reacting the matrix under heterogenic conditions (where the matrix remains insoluble in the reaction medium) with reactive molecules that can react with one or more of the groups on the construct such as hydroxyl groups, remaining aldehyde groups, amino groups, or carboxylic acid groups. Examples of reactive groups are fatty amines, glucosamines, amino acids, and hydroxylamines that react with the available aldehydes or carboxylic acid on the construct; isocyanate containing molecules and carboxylic acid molecules are attached by a urethane, urea, or ester bonds with either the hydroxyl or amino groups on the construct. Another chemical modification is the addition of another crosslinking agent that acts as a crosslinker by forming an ester, ether or urethane bond. For example, hexamethylenediisocyanate solution in tetrahydrofuran (THF, 0.5 to 5% w/v) with or without a catalyst (organo stannous catalysts) is added to the polysaccharide construct and allowed to react for a few hours before the construct is washed with THF and ethanol to remove the non-reacted isocyanate molecules. In another example a solution of 1,2–7,8-diepoxyoctane (available from Aldrich) in THF or in acetone is reacted with the construct at about 50° C. with acidic catalysis to form etheric crosslinking bonds.

The following examples demonstrate the above modifications:

PLA Coating of Chitosan—AG Matrices

Chitosan-AG matrices were dipped in a solution of PLA (molecular weight of 30,000) in chloroform (4% or 8%) for a fixed amount of time (5, 15 or 30 minutes). The matrices were air-dried at room temperature, and the change in their weight was monitored. The loaded amounts of PLA on the Chitosan-AG constructs are given in the tables below:

Matrices Containing 5% AG in Chitosan

| % PLA | Dipping time | Inital weight (g) | Final weight (g) | % Coating (coat w./finalw.) |
|---|---|---|---|---|
| 4% | 5 min | 0.0110 | 0.0188 | 40 |
| 4% | 15 min | 0.0136 | 0.0229 | 41 |
| 4% | 30 min | 0.0060 | 0.0113 | 47 |
| 8% | 5 min | 0.0121 | 0.0380 | 68 |
| 8% | 15 min | 0.0106 | 0.0284 | 63 |
| 8% | 30 min | 0.0129 | 0.0287 | 65 |

Matrices Containing 10% AG in Chitosan

| % PLA | Dipping time | Initial weight (g) | Final weight (g) | % Coating |
|---|---|---|---|---|
| 4% | 5 min | 0.0155 | 0.0371 | 48 |
| 4% | 15 min | 0.0188 | 0.0327 | 43 |
| 4% | 30 min | 0.0123 | 0.0234 | 47 |
| 8% | 5 min | 0.0181 | 0.0325 | 64 |
| 8% | 15 min | 0.0112 | 0.0301 | 63 |
| 8% | 30 min | 0.0096 | 0.0263 | 63 |

Matrices Containing 20% AG in Chitosan

| % PLA | Dipping time | Initial weight (g) | Final weight (g) | % Coating |
|---|---|---|---|---|
| 4% | 5 min | 0.0134 | 0.0251 | 47 |
| 4% | 15 min | 0.100 | 0.0189 | 47 |
| 4% | 30 min | 0.0144 | 0.0226 | 46 |
| 8% | 5 min | 0.0125 | 0.0333 | 62 |
| 8% | 15 min | 0.0161 | 0.0401 | 60 |
| 8% | 30 min | 0.0117 | 0.0298 | 61 |

The matrices increased in weight by about 45% from the 4% polymer solution and about 60% for the 8% w/v solution with no effect on the incubation time. The matrices remained in their shape, but they became harder.

Swelling of coated gels was determined in order to see if the coating changed the matrices ability to swell in water. The coated matrices were put in water, and their weight was checked after half an hour in water.

% of Water Content of Coated Matrices After ½ Hour in Water

| % AG | % PLA | Dry weight (g) | Swollen weight (g) | % swelling |
|---|---|---|---|---|
| 5 | 67 | 0.0284 | 0.1455 | 80 |
| 10 | 65 | 0.0301 | 0.1296 | 77 |
| 20 | 68 | 0.0401 | 0.1641 | 75 |

The results suggest the coated matrices absorb water and the coating did not significantly affect the water uptake. Non-coated matrices absorb more than 90% of water after the same amount of time. The matrices were seeded with cells and did show good adherence and proliferation of cells.

Synthesis of Chitosan—Arabinogalactan Crosslinked Spheres

P2TE-78: A 4% solution of chitosan in 5% aqueous acetic acid containing 2% NaCl was prepared, and 6 g of this solution were mixed with a solution of 0.1 g oxidized AG in 2.5 ml Borate buffer pH=8.5. The chitosan-AG mixture was dispersed in a mixture of 35 ml of liquid paraffin and 25 ml of petroleum ether containing 0.43 g ($1.05 \times 10^3$ mole) of sorbitan-monostearate (span 60,HLB=4.7) at room temperature. The dispersion was stirred at 2,000 rev/min overnight. At the end of the reaction, the hardened particles were washed 3 times with petroleum-ether, followed by methanol, and finally with acetone, then the particles were air-dried for a few hours at room temperature. Finally, the particles were swollen in water overnight, and then lyophilized.

Result: Powder with orange color is obtained. In water, the particles are not soluble, a suspension is obtained. Particles size: 420–250 μM. Available weight: 0.1 g.

As a further note regarding sample P2TE-65 if as the final step of the process the particles are swollen in water overnight and then lyopbilized there is the following resultant product.

Result: Powder with an orange color is obtained. In water the particles are not soluble; a suspension is obtained. The particle size is 420–250μM. The available weight is 0.2 g.

P2TE-79: A 4% solution of chitosan in 5% aqueous acetic acid containing 2% NaCl was prepared, and 6 g of this solution were mixed with a solution of 0.1 g oxidized AG in 2.5 ml Borate buffer pH=8.5. The chitosan-AG mixture was dispersed in a mixture of 35 ml of liquid paraffin and 25 ml of petroleum ether containing 1.1 g($1.05 \times 10^{-3}$ mole) of sorbitan-sesquioleate (arlacel 83, HLB=3.7) at room temperature. The dispersion was stirred at 2000 rev/min overnight. At the end of the reaftion, the hardened particles were washed 3 times with petroleum-ether, followed by methanol, and finally with acetone, then the particles were air-dried for a few hours at room temperature. Finally, the particles were swollen in water overnight, and then lyophilized.

Result: Powder with orange color is obtained. In water, the particles are not soluble, a suspension is obtained. Particles size: 420–250 μM. Available weight: 0.1 g.

| % AG | % PLA | Dipping Time | Dry Weight (g) | % Swelling (after 2 h) | % Swelling (after 48 h) |
|---|---|---|---|---|---|
| 10 | 10 | 15 min | 0.0145 | 78 | 84 |
| 10 | 20 | 15 min | 0.0143 | 78 | 81 |
| 10 | 40 | 15 min | 0.0177 | 76 | 75 |
| 20 | 10 | 15 min | 0.0111 | 84 | 88 |
| 20 | 20 | 15 min | 0.0115 | 56 | 74 |
| 20 | 40 | 15 min | 0.0451 | 50 | 64 |

The results suggest the coated matrices absorb water. Non-coated matrices arrive to more than 90% swelling after the same amount of time, but it could be that the coating is only slowing the rate of swelling, and is not decreasing it, however, the water content of coated matrices is high.

PLGA Coating of Chitosan—AG Matrices

Chitosan-AG matrices were dipped in a solution of PLGA in chloroform (5%, 10%, 20% or 40%) for a fixed amount of time (15 minutes). The matrices were air-dried at room temperature, and the change in their weight was observed in order to determine if the matrices have been coated.

Matrices Containing 10% AG in Chitosan

| % PLGA | Dipping Time | Initial weight (g) | Final weight (g) | % Increase (coat w./initial w.) | % Coating (coat w./final w.) |
|---|---|---|---|---|---|
| 10% | 15 min | 0.2803 | 0.6917 | 147 | 59 |
| 20% | 15 min | 0.2749 | 0.8761 | 219 | 69 |
| 40% | 15 min | 0.2546 | 1.1888 | 367 | 78 |

Matrices Containing 20% AG in Chitosan

| % PLGA | Dipping Time | Initial weight (g) | Final weight (g) | % Increase (coat w./initial w.) | % Coating (coat w./final w.) |
|---|---|---|---|---|---|
| 10% | 15 min | 0.2728 | 0.3501 | 128 | 56 |
| 20% | 15 min | 0.2603 | 0.6584 | 253 | 71 |
| 40% | 15 min | 0.26 | 1.361 | 523 | 84 |

The matrices remained in their shape, but they became harder.

Swelling of coated gels was determined in order to see if the coating changed the matrices ability to swell in water.

The coated matrices were put in water, and their weight was checked after 2 h, and 48 h.

% of water content of coated matrices is the amount of water absorbed in the polymer construct after coating with PLGA.

3. Applications

These matrices can be applied for surgical hemeostatic materials, adhesion prevention and as wound healing bandages. For these applications the shape and properties of the device has to fit the specific application. Hemeostatic materials should be very porous, flexible, have high capacity for absorbing body fluids, retain their shape for hours or a few days and then degrade and eliminate during the next few days. The device of this invention can have the properties of the standard surgical materials such as Oxicel and Gelfoam which are used routinely as hemostates in various surgical procedures including in the brain.

Wound Healing

The chitosan-arabinogalactan cross-linked polymers can be used as topically applied agents in the form of sheets or powder to facilitate wound-healing. The polymers can be shaped to fill hollow cavities after surgery. The polymers may be shaped and used per se or can be employed as a scaffold on which cells are grown and then used for transplantation. The polymers are expected to be particularly beneficial for facilitating the healing of bums. When used as wound healing agents, the polymers may include antibiotics as well as other antiseptic agents. Further, the polymers may incorporate other medicaments which facilitate wound healing.

For wound healing the requirements are similar with respect to application on the wound, biodegradation and elimination. For wound healing where the bandage is used as a barrier, it should have certain properties of oxygen, gas and water transport.

Tissue Adhesion Prevention

For use as tissue adhesion prevention agents, the polymer compositions can be used to prevent adhesion of tissue to bone or tissue to tissue such as in gynecological surgery and abdominal surgery.

The chitosan-arabinogalactan crosslinked polymers can be made to take on various shapes such as slabs, rods, sheets, thin films and microspheres. For use as agents to prevent tissue adhesion, the polymers may take the form of slabs, sheets, thin films and powder in the form of microspheres. The polymers can be used for tissue culture in the form of slabs, sheets and microspheres. The polymers can be shaped to form scaffolds upon which cells are grown and then implanted into the body as a tissue replacement.

The employing of polymers to prevent tissue-adhesion is disclosed in U.S. Pat. Nos. 5,410,016 and 5,462,990 to Hubbell et al and 5,480,436 to Bakker et al.

For the adhesion prevention device, porous films or fabric shape material which are soft and gentle without sharp edges can be placed between organs during surgical procedures. The matrix should retain its physical barrier properties to reduce the adhesions between internal organs and should degrade slowly after about one week in place. During this period the healing process of the affected surface will take place while the polymer degrades and is eliminated from the site. As shown above, the flexibility, water absorption, degradation time and other desired properties can be tailored for the specific application by physically or chemically modifying the polysaccharide matrix.

Effect-prolonging Agents

The inventors contemplate using the polymers of this invention as effect-prolonging agents wherein therapeutic agents such as antibiotics, analgesics and anti-inflammatory agents are added to the polymer and then formulated into a dosage-form.

Cell Culture Media

The inventors have found that the microspheres and sheets can be used to culture chondrocytes as well as other cells.

CROSSLINKING OF DEXTRAN AND ARABINOGALACTAN

Crosslinked gels were prepared from two representative polysaccharides: Dextran, a linear 1,6-a-D-glucans with an average molecular weight of 40 kd and Arabinogalactan (AG), a highly branched 1,3-poly(Arabinose-galactose) of 20 kd average molecular weight. The polysaccharides were oxidized with increasing amounts of $KIO_4$ in water to yield the polyaldehyde derivatives. Oxidation of Dextran with a 1:1 saccharide:$KIO_4$—mole ratio yielded 50% oxidation of the saccharide groups with a decrease in molecular weight.

Reaction at a lower ratio of $KIO_4$ resulted in fewer aldehyde groups and fewer chain scissions. To the contrary, when AG was oxidized under the same conditions, less oxidation with minimal changes in the polymer molecular weight were observed. AG oxidized with AG:$KIO_4$ 1:1 molar ratio yielded about 38% oxidized saccharide units along the polymer chain with minimal change in molecular weight.

The oxidized polymers were reacted with increasing amounts of di- or multi amino groups such as ethylene diamine, lysine or proteins (Albumin or Gelatin) to obtain branched or crosslinked polymers. Oxidized Dextran formed a branched polymer with molecular weights of up to 500,000 when reacted with up to 15% w/w lysine or 100% w/w proteins. Oxidized AG was reacted with these amines at low w/w ratios (1% lysine or 50% proteins) a crosslinked polymer was obtained which absorbed 100–400% water depending on the degree of crosslinking. Concentrated basic solution of extensively oxidized AG (10–15% w/w) was self crosslinked forming acetals and hemiacetals bonds when reacted at 37° C. for 24 h. pH responsive gels were prepared from the reaction of oxidized AG (32%) with glutamic acid (20% w/w) and lysine (1% w/w). The carboxylic acid rich gel swelled to about 150% at pH2 and 300% at pH12.

Preparation of Chitosan-AG Spheres

A 4% solution of chitosan in 5% aqueous acetic acid containing 2% NaCl was prepared. In a separate container a 30% w/v of oxidized arabinogalactan (AG, 32% of the saccharide rings were oxidized) was prepared. To the chitosan solution, increasing amounts of oxidized AG solution was added (10 % to 50% w/w AG) and the solution was mixed to form a uniform clear solution. 6 g of this solution were dispersed in a mixture of 35 ml of paraffin oil and 25 ml of petroleum ether containing various amounts (0.2 to 1.0 g) of Span 20. The dispersion was stirred using a stainless steel paddle stirrer at 1000 rpm for about 6 hours where microparticles were formed. The hardened particles were collected by filtration and washed several times with petroleum ether, diethyl ether, acetone and dried by air evaporation. Particles of sizes from 50 to 500 microns were obtained depending on the amount of surfactant and the ratio between AG and chitosan. The amine derivative was obtained by reduction of the beads with sodium borohydride in water for 2 hours at room temperature.

Hydrophobization of the Beads

To increase the hyrophobic nature of the gel and obtain gels that absorbe less water and degrade for a longer period, hydrophobic side groups were conjugated or inserted in the polymer martix during the gel preparation or modification of the already formed matrices.

Beads were prepared from these hydrophobized AG as described above. Additional uses for these polysaccharide gels:

1. adhesion prevention—the gel is prepared as a fabric or solution and used for preventing adhesion after surgical procedure.
2. wound healing and bandages.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A polymer of chitosan cross-linked with arabinogalactan.

2. Microspheres composed of a polymer of chitosan cross-linked with arabinogalactan of claim 1.

3. Microbeadlets prepared from a polymer of chitosan cross-linked with arabinogalactan or a polymer of dextran cross-linked with arabinogalactan.

4. A wound healing or tissue adhesion preventing device comprising chitosan cross-linked with arabinogalactan or the polymer of dextran cross-linked with arabinogalactan.

5. The reaction product of an oxidized polysaccharide cross-linked with a polyamine wherein the oxidized polysaccharide is a member of the group consisting of arabinogalactan, pullulan, cellulose and amylose at an oxidation degree of from 5% to about 50% of the saccharide groups and the polyamine is selected from the group consisting of amino containing polysaccharides, synthetic polyamines, collagen, fibrinogen, fibrin, albumin, hydrolyzed proteins, chitosan, poly(ethylene imine), and poly (vinyl amine).

6. A polymer product comprising a polysaccharide cross-linked with an amine or a protein wherein the amine or protein is collagen, fibrinogen, fibrin, albumin, hydrolyzed protein or chitosan.

7. The polymer product of claim 6 wherein the polysaccharide is arabinogalactan, pullan, cellulose or amylose.

8. The polymer product of claim 6 wherein the amine is poly (ethylene imine) or poly (vinyl amine).

9. The polymer of claim 6 wherein the polysaccharide is oxidized.

\* \* \* \* \*